United States Patent [19]

Grisar et al.

[11] 3,931,155

[45] Jan. 6, 1976

[54] PROCESS FOR PREPARING 2-AZACYCLOALKYLMETHYL KETONES

[75] Inventors: J. Martin Grisar; George P. Claxton, both of Cincinnati, Ohio

[73] Assignee: Richardson-Merrell Inc., Wilton, Conn.

[22] Filed: Apr. 25, 1973

[21] Appl. No.: 354,206

[52] U.S. Cl. ............ 260/240 J; 424/248; 424/250; 424/267; 424/274; 424/272; 260/240 R; 260/293.57; 260/293.58; 260/293.59; 260/293.6; 260/293.8; 260/326.5 D; 260/326.5 J; 260/326.5 SA; 260/330.5
[51] Int. Cl.² ........................................ C09B 23/00
[58] Field of Search...... 260/240 CA, 240 R, 239 B, 260/326.5 R, 293.8, 330.5, 293.57, 293.58, 293.6, 326.5 D, 325.5 J, 326.5 SA, 240 J

[56] References Cited
UNITED STATES PATENTS

| | | | |
|---|---|---|---|
| 3,316,272 | 4/1967 | Roberts et al. | 260/240 CA |
| 3,853,855 | 12/1974 | Grisar et al. | 260/240 R |
| 3,882,104 | 5/1975 | Grisar et al. | 260/240 CA |

OTHER PUBLICATIONS

Claxton et al., J. Med. Chem., Vol. 15, pp. 500 to 503 (1972).

Uhlemann, Chemical Abstracts, Vol. 56, Col. 10092 (1962).

*Primary Examiner*—John D. Randolph
*Attorney, Agent, or Firm*—William J. Stein; Eugene O. Retter; George W. Rauchfuss, Jr.

[57] ABSTRACT

A process for the preparation of 2-azacycloalkylmethyl ketones by chelating a methyl ketone with magnesium methyl carbonate and condensing the chelate with a 1-azacycloalkene in an atmosphere of carbon dioxide. The novel compounds described are useful anticoagulants.

11 Claims, No Drawings

PROCESS FOR PREPARING 2-AZACYCLOALKYLMETHYL KETONES

DISCUSSION OF PRIOR ART

The reaction of β-ketoacids with 2,3,4,5-tetrahydropyridines under "physiological" conditions to establish pathways of plant alkaloid biosyntheses has been explored by Schöpf and co-workers, Liebigs Ann. Chem. 626, 123 (1959). Heretofore a synthetic application of this reaction has been limited due to the lack of water solubility of many of the β-ketoacids and the difficulty in obtaining suitable starting materials. Furthermore, the self-condensation of 2,3,4,5-tetrahydropyridine requires that this reaction be conducted under limited and carefully controlled conditions, cf., Schöpf et al., Liebigs Ann. Chem., 559, 1 (1948) and Wisse et al., Rec. Trav. Chem. Pays-Bas. 82, 763 (1963). The conversion of ketones to β-ketoacids using magnesium methyl carbonate has been described by Stiles, J. Am. Chem. Soc. 81, 2598 (1959).

We have previously reported the preparation of a 2-azacycloalkylmethyl ketone, namely, 4′-(fluoren-9-ylidenemethyl)-2-(2-piperidyl)acetophenone, by means of the novel process of this invention, Claxton et al., J. Med. Chem. 15, 500 (1972). To applicants' knowledge no other publications are known which disclose the synthesis of 2-azacycloalkylmethyl ketones by means of the improved modification of the Schöpf reaction described herein.

SUMMARY OF THE INVENTION

This invention relates to a novel process for preparing 2-azacycloalkylmethyl ketones. More particularly, this process relates to the preparation of 2-azacycloalkylmethyl ketones by condensing a magnesium chelate of a methyl ketone with a 1-azacycloalkene. Still more particularly, this process relates to the preparation of 2-azacycloalkylmethyl ketones having the formula:

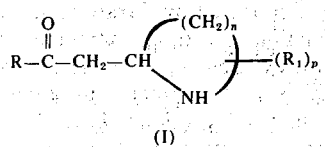

(I)

wherein $n$ is an integer of from 3 to 5, $p$ is an integer of from 1 to 2, R is a neutral organic radical and $R_1$ is hydrogen or a lower alkyl having from 1 to 4 carbon atoms, which comprises heating a solution of a methyl ketone having the formula

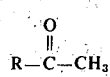

with an excess of magnesium methyl carbonate to form a magnesium chelate; cooling the reaction mixture and reacting said chelate solution in an atmosphere of carbon dioxide with a 1-azacycloalkene having the formula:

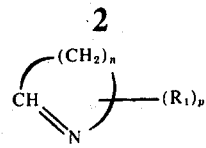

and isolating the product therefrom.

The process of this invention is useful in the preparation of novel organic compounds which belong to a class of methyl ketones in which the methyl group is substituted with an azacycloalkane moiety in the 2-position of the azacycloalkane ring. Various groups of 2-azacycloalkylmethyl ketones which are described herein as well as their corresponding alcohols are useful as anticoagulants in preventing blood platelet aggregation.

DETAILED DESCRIPTION OF THE INVENTION

Previous attempts to prepare 2-azacycloalkylmethyl ketones in which the 2-azacycloalkyl ring is 2-piperidine by means of a catalytic reduction of the corresponding 2-pyridylmethyl ketones resulted in poor yields. In addition a partial reduction of the pyridine ring occurs as well as a concomitant reduction of both the carbonyl oxygen and the double bond in the 9-position of the fluorene ring. In an attempt to overcome these difficulties and at the same time obtain a more general procedure for the preparation of 2-azacycloalkylmethyl ketones, applicants investigated a large number of reagents and reaction conditions.

The work of Schöpf and co-workers with 2,3,4,5-tetrahydropyridine and β-ketoacids in aqueous solutions to form the corresponding 2-piperidylmethyl ketones has, unfortunately, not found wide application for synthetic chemists and has been restricted in its use, due to reasons of solubility, primarily to the lower alkanoyl and benzoylacetic acids. In addition to the unavailability and the lack of solubility of the more complex β-ketoacids, the 2,3,4,5-tetrahydropyridine reagent tends to condense with itself and consequently, the reaction requires a close pH control. Preferably, the Schöpf reaction is conducted at a pH of less than 10 to minimize self-condensation and to minimize various additional side reactions from occurring.

Applicants have discovered a modification of the Schöpf reaction which permits the condensation of a wide variety of β-ketoacids with 2,3,4,5-tetrahydropyridine and which, in addition, enables condensation to occur not only with 2,3,4,5-tetrahydropyridine but with a variety of additional azacycloalkenes. Furthermore, our novel process obviates the need for pH control and overcomes the limitations of water solubility that are inherent in the Schöpf reaction.

The instant process consists essentially of the reaction of a methyl ketone with magnesium methyl carbonate (MMC) in solution to form a magnesium chelate. The resulting chelate is condensed in an atmosphere of carbon dioxide with a 1-azacycloalkene or a substituted 1-azacycloalkene at moderate or ambient temperatures and the resulting 2-azacycloalkylmethyl ketone which is obtained is isolated as its acid addition salt or as its free base by precipitation or extraction procedures. This reaction is schematically represented as follows in which the symbols $n$, $p$, R and $R_1$ have the values given above.

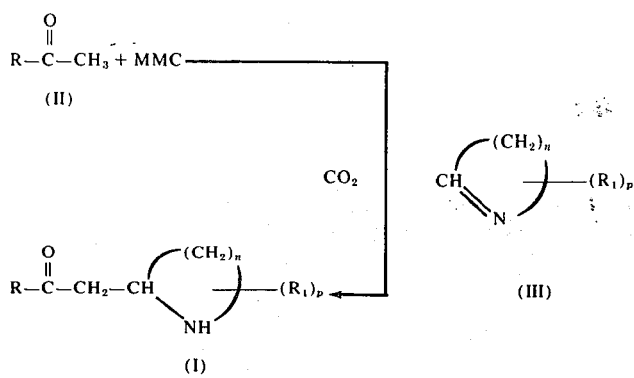

The MMC reagent is prepared by the addition of magnesium turnings to dry methanol until all of the metal is converted to magnesium methoxide. A solvent such as dimethylformamide is added and the stirred solution saturated with dry carbon dioxide as described by H. L. Finkbeiner and M. Stiles, J. Am. Chem. Soc., 85, 616 (1963). When a methyl ketone is permitted to react with a large excess of this reagent, a chelate results which is believed to have the formula:

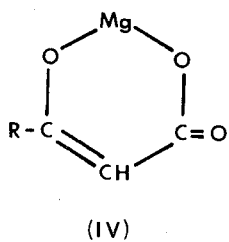

(IV)

Generally, a 2 to 6 molar excess of the MMC reagent is employed at a temperature ranging from 80° to 120°C. Preferably an excess of 4 moles of MMC reagent is used for chelation at the higher temperatures. The methanol that is formed is removed by sweeping a stream of an inert gas, such as nitrogen, over the hot solution. After a period of time ranging from 2 to 36 hours the chelate solution is permitted to cool and the inert gas is replaced with carbon dioxide. The solution is saturated with carbon dioxide and a carbon dioxide atmosphere is maintained throughout the condensation of the chelate with the 1-azacycloalkene.

To the magnesium chelated methyl ketone solution is added a one molar equivalent or slight excess of 1-azacycloalkene with stirring. In general the condensation is effected by stirring the reaction mixture at ambient temperatures. The preferred reaction solvent is dimethylformamide since the MMC reagent is ordinarily prepared therein. On occasion it may be advantageous to add an additional inert solvent to the reaction mixture if, for example, the reaction is to be conducted at a temperature of less than −61°C., the freezing point of dimethylformamide. It is further practicable to precipitate the magnesium chelate by the addition of large amounts of ether and to dissolve or suspend the precipitated chelate in other inert solvents. Suitable solvents include tetrahydrofuran, benzene or dimethylacetamide.

Condensation takes place at temperatures ranging from −50° to 100°C. Preferably the reaction is conducted at temperatures ranging from 0°-60°C. both as a matter of convenience and since elevation of the reaction temperature above 100°C. results in diminished yields.

The reaction time varies from a few hours to several weeks depending upon the reaction temperature and the nature of the reactants, particularly with respect to the degree of steric hindrance of the acetyl group of the methyl ketone (II), Inasmuch as the reaction is conducted and remains a homogenous solution until completion, the duration of the reaction can readily be extended for several weeks. Preferably the reaction is conducted in a period of from 16 to 60 hours.

Of particular importance to the successful operation of this reaction is the maintenance of an appropriate atmosphere. Some success is obtained under normal atmospheric conditions, particularly in the presence of a small amount of moisture. Under anhydrous conditions in an atmosphere of nitrogen, however, no product is obtained. Consistently good yields result when the condensation is carried out in an atmosphere of carbon dioxide.

The desired products of this invention are isolated by pouring the reaction mixture into an excess of dilute acid. Preferably a mixture of 2 to 12 normal hydrochloric acid and ice is employed. When the acid addition salt of the desired 2-azacycloalkylmethyl ketone precipitates, it is collected by filtration. Alternatively, the acidified reaction mixture is extracted with a suitable solvent, as for example, chloroform or methylene chloride, and the solvent extract evaporated, leaving the desired product as a residue. It is also possible, but generally more cumbersome, to treat the acidified reaction mixture with a base such as sodium hydroxide until alkaline. The desired product can then be extracted using an appropriate solvent from the alkaline slurry containing precipitated magnesium hydroxide. In either event the crude products are readily purified by recrystallization of their acid addition salts using ordinary solvents or solvent mixtures.

The 1-azacycloalkenes, represented by the Formula (III), which can be condensed with a magnesium chelated methyl ketone are defined by the symbol $n$ to include 5,6 and 7 membered heterocyclic rings which are monounsaturated at the 1-position. Thus, when $n$ is an integer of from 3 to 5 and $R_1$ is hydrogen, the corresponding heterocycles: 1-pyrroline, 2,3,4,5-tetrahydropyridine and 3,4,5,6-tetrahydro-2H-azepine are delineated. These heterocycles may be further substituted as when the symbol $R_1$ represents lower alkyl. The term lower alkyl includes members having from 1 to 4 carbon atoms. Illustrative members of this group include the radicals, methyl, ethyl, propyl, isopropyl, butyl, sec.-butyl and t-butyl. The heterocycles may be either mono or di-substituted as indicated by the symbol p. When di-substituted, the lower alkyl radicals may be substituted either on the same carbon atom or on different carbon atoms. Substitution on the unsaturated carbon is excluded, however, as illustrated by the presence of a hydrogen atom in Formula (III). Thus, for example, 6-methyl-2,3,4,5-tetrahydropyridine and 2-phenyl-1-pyrroline were found not to undergo condensation.

It is important to note that the 1-azacycloalkenes can exist as trimers, as for example, the trimers of 1-pyrroline and 2,3,4,5-tetrahydropyridine. In the case of the latter compound it can exist in two isomeric forms that are known as α and β-tripiperidein. In solution these trimers readily depolymerize to their monomers in a manner similar to the well known behavior of formaldehyde. However, under alkaline aqueous conditions 2,3,4,5-tetrahydropyridine undergoes an irreversible self-condensation to form γ-tripiperidein. This self-condensation does not occur using the process of the present invention.

Illustrative 1-azacycloalkenes as indicated in Formula (III) above which are useful in the instant process include: 1-pyrroline, 3-methyl-1-pyrroline, 5,5-dimethyl-1-pyrroline, 3-propyl-2,3,4,5-tetrahydropyridine, 4-t.-butyl-2,3,4,5-tetrahydropyridine, 3,5-diethyl-2,3,4,5-tetrahydropyridine, 3,4,5,6-tetrahydro-2H-azepine, and 2,2-dimethyl-3,4,5,6-tetrahydro-2H-azepine.

Any methyl ketone in which the radical R is a neutral organic substituent (III) is capable of chelation with MMC and of subsequent condensation with the aforementioned 1-azacycloalkenes. However, in order for condensation to occur, it is essential that the starting material be a methyl ketone. Attempts to condense a number of non-methyl ketones, including some which are known to chelate with MMC and form β-ketoacids, were without success.

The methyl ketones employed herein are obtained by methods well known to the art. For example, the alkyl methyl ketones are obtained by oxidation of the corresponding secondary alcohols. Aryl methyl ketones can be prepared using a Friedel-Crafts acetylation of the aromatic ring with acetyl chloride or acetic anhyride and a catalyst such as aluminum chloride in an appropriate solvent. Certain aryl methyl ketones can be obtained by the reaction of o, m or p-hydroxyacetophenone with an arylalkyl or aryloxyalkyl halide. Compounds in which the R radicals contain one or more double bonds of particular interest in that these compounds cannot be readily prepared by alternative methods such as reduction. Illustrative of the various neutral organic radicals represented by the symbol R are: alkyl, cycloalkyl, alkenyl, phenyl, substituted phenyl, phenylalkyl, phenylalkylene, diphenylalkyl, diphenylalkylene, tricycloaryl, and a variety of heterocycles. Additionally the various aromatic rings may be further substituted with such substituents as alkyl, cycloalkyl, alkoxy, halogen, phenyl, phenoxy, phenylalkyl, phenylalkoxy, phenoxyalkyl, phenoxyalkoxy, thiomethyl, thiophenyl, trifluoromethyl, cyano and dimethylsulfamoyl.

The radical represented by the symbol R is limited in that it must represent a neutral organic radical in order not to react with the MMC reagent. Thus, substituents such as amino, nitro, carboxylic acid, sulfonic acid and phenolic-hydroxy groups are undesirable substituents in carrying out the instant reaction. Additionally, sterically hindered compounds are somewhat more difficult to react, but can be reacted under forced conditions as illustrated in Example III. The term neutral organic radical as used throughout the specification and claims is limited to those radicals which are specifically identified in the structures enumerated as (1) to (8) below. More particularly these radicals are selected from the group consisting of alkyl, alkenyl, carbocycle and aromatic heterocycles, as for example, furan, pyrrole, benzothiophene, pyrazole, oxazole, benzimidazole, dibenzofuran and dibenzothiophene.

Illustrated below are examples of various classes of 2-azacycloalkylmethyl ketones which can be prepared in accordance with the process of this invention. In the following illustrations the symbols $n$, $p$ and $R_1$ have the values previously assigned.

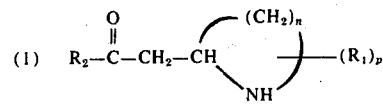

in which $R_2$ is selected from the group consisting of alkyl having from 1 to 24 carbon atoms; cycloalkyl having from 3 to 12 carbon atoms, alkenyl having from 2 to 24 carbon atoms, phenylalkyl having from 1 to 8 carbon atoms, and the pharmaceutically acceptable acid addition salts thereof.

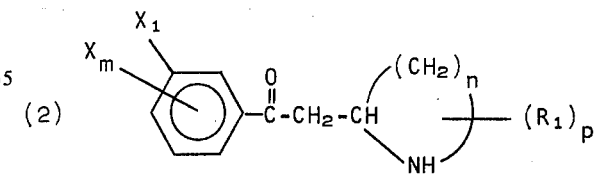

in which $m$ is an integer of from 1 to 3; X is selected from the group consisting of alkyl having from 1 to 20 carbon atoms, alkoxy having from 1 to 16 carbon atoms; alkylthio having from 1 to 16 carbon atoms; cycloalkyl having from 5 to 7 carbon atoms, halogen, trifluoromethyl, cyano and dimethylsulfamoyl; $X_1$ is hydrogen or when taken together and adjacent to the group X is selected from the group of cyclic radicals consisting of $-(CH_2)_3-$, $-(CH_2)_4-$, $-C(CH_3)_2CH_2CH_2C(CH_3)_2-$, and $-CH=CH-CH=CH-$, and the pharmaceutically acceptable acid addition salts thereof.

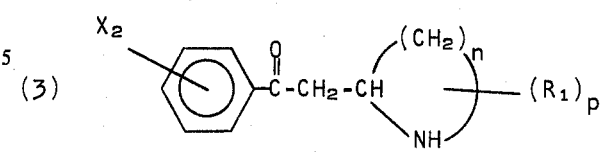

in which $X_2$ is selected from the group consisting of phenyl, halophenyl, trifluoromethylphenyl, alkoxyphenyl having from 1 to 4 carbon atoms, alkylthiophenyl having from 1 to 4 carbon atoms, phenoxy, halophenoxy, trifluoromethylphenoxy, alkoxyphenoxy having from 1 to 4 carbon atoms, alkylthiophenoxy having from 1 to 4 carbon atoms, phenylthio, phenylalkyl having from 1 to 4 carbon atoms, phenylvinyl, phenylalkoxy having from 2 to 4 carbon atoms, phenoxyalkoxy having from 2 to 4 carbon atoms, and the pharmaceutically acceptable acid addition salts thereof.

in which Y is carbon or nitrogen; Z is selected from the group consisting of oxygen, sulfur or $NR_3$; $R_3$ is selected from the group consisting of alkyl having from 1 to 12 carbon atoms, cycloalkyl having from 5 to 7 carbon atoms, phenyl, mono-, di- and trialkylphenyl having from 1 to 4 carbon atoms, mono-, di- and trialkoxyphenyl having from 1 to 4 carbon atoms and halophenyl; $X_4$ is attached to a carbon atom and is selected from the group consisting of hydrogen and lower alkyl having from 1 to 4 carbon atoms; $X_5$ is hydrogen or when taken together and adjacent to the group $X_4$ is the (4) 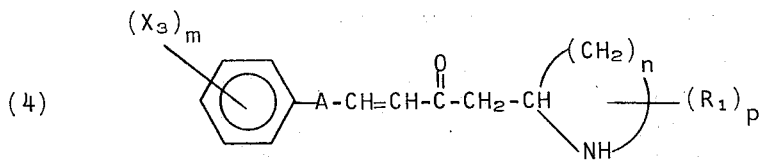

in which $m$ is an integer of from 1 to 3; $X_3$ is selected from the group consisting of hydrogen, lower alkyl having from 1 to 6 carbon atoms, alkoxy having from 1 to 6 carbon atoms, alkylthio having from 1 to 6 carbon atoms, halogen, trifluoromethyl and phenyl; A is a sigma bond, or selected from the group of radicals consisting of vinylidene and propenylidene, and the pharmaceutically acceptable acid addition salts thereof.

cyclic radical —CH=CH—CH=CH; and the pharmaceutically acceptable acid addition salts thereof.

(6) 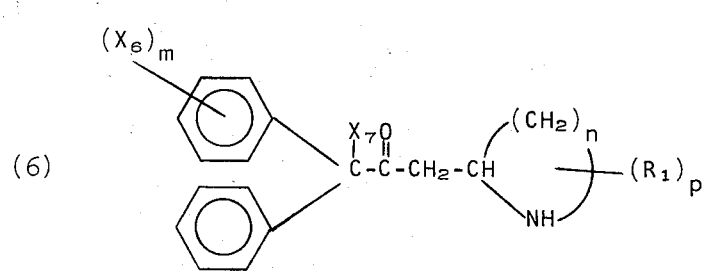

in which $m$ is an integer of from 1 to 3; $X_6$ is selected from the group consisting of hydrogen, lower alkyl having from 1 to 4 carbon atoms, lower alkoxy having from 1 to 4 carbon atoms, alkylthio having from 1 to 4 carbon atoms and halogen; $X_7$ is selected from the group consisting of hydrogen and lower alkyl having from 1 to 4 carbon atoms; and the pharmaceutically acceptable acid addition salts thereof.

(5) 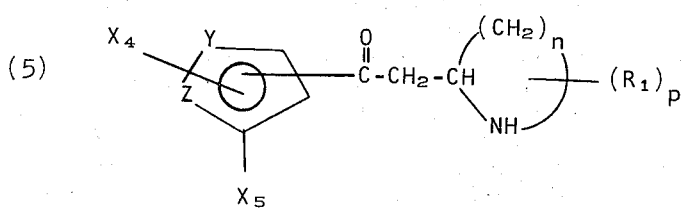

and

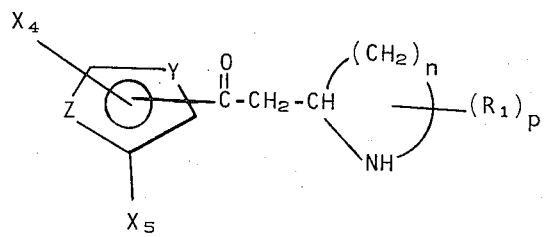

(7) 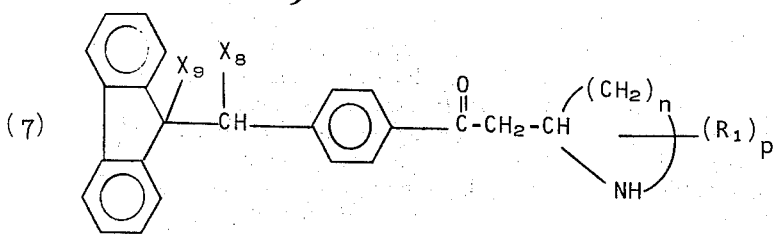

in which $X_8$ and $X_9$ are hydrogen and when taken together form a bond between the carbon atoms to which they are attached; and the pharmaceutically acceptable acid addition salts thereof.

(8) 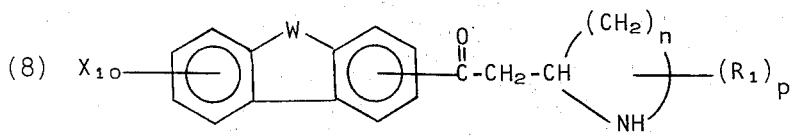

in which $X_{10}$ is selected from the group consisting of hydrogen, lower alkyl having from 1 to 4 carbon atoms, lower alkoxy having from 1 to 4 carbon atoms and halogen; W is selected from the group of radicals consisting of —O—, —S—, —CH$_2$—, —CH=CH— and —CH$_2$CH$_2$—; and the pharmaceutically acceptable acid addition salts thereof.

The compounds claimed herein, their preparation conversion to the alcohols, and the usefulness as anticoagulants of both the novel ketones and their corresponding alcohols is more fully illustrated by means of a closer examination of this last class of compounds (8). Both the 2-azacycloalkylmethyl tricyclic arylalkylene alcohols and ketones can be represented by the general formula:

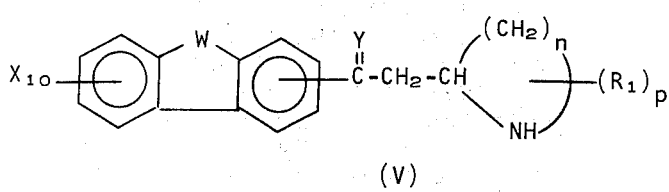

(V)

wherein the symbols $n$, $p$, $R_1$, W and $X_{10}$ have the values previously assigned and the symbol Y represents the radicals =O or

As seen by an examination of Formula (V), this class of compounds share in common a 2-azacycloalkylmethyl moiety and a substituted tricyclic arylalkylene radical, both of which are attached to the keto or carbinol function of the molecule.

The azacycloalkylmethyl moieties include the 5,6 and 7-membered nitrogen containing saturated heterocyclic rings are defined by the symbol $n$. Thus, when n is an integer of from 3 to 5 and $R_1$ is hydrogen, the corresponding heterocycles, 1-pyrrolidine, piperidine and 2,3,4,5,6,7-hexahydro-1H-azepine, are delineated. These heterocycles may be further substituted as illustrated by the symbol $R_1$, which may represent a lower alkyl group in addition to hydrogen. The term "lower alkyl" includes members having from 1 to 4 carbon atoms. Illustrative members of this group include the radicals methyl, ethyl, propyl, isopropyl, butyl, sec.-butyl and t-butyl. The 2-azacycloalkyl rings may be either mono or di-substituted as indicated by the symbol $p$. When di-substituted, the lower alkyl radicals may be substituted either upon the same carbon atom or upon different carbon atoms. Further substitution in the 2-position, however, is precluded as illustrated by the presence of a hydrogen atom in Formula (V) above. Thus, for example, 6-methyl-2,3,4,5-tetrahydropyridine and 2-phenyl-1-pyrroline were found not to undergo condensation.

The terminal tricyclic aryl radicals which are encompassed within the scope of the present invention include the tricyclic rings: fluorene, phenanthrene, 9,10-dihydrophenanthrene, dibenzofuran and dibenzothiophene, as represented by the symbol W in Formula (V) above. As indicated, these tricyclic rings are attached at any one of three positions in the aromatic portion of the molecule. The tricyclic aryl radical can be unsubstituted as when the symbol $X_{10}$ represents hydrogen, or it may be mono-substituted with a lower alkyl group or a lower alkyl ether in any one of the three positions of the remaining fully aromatic portion of the molecule. The term "lower alkyl" includes members having from 1 to 4 carbon atoms. Illustrative members of this group include the radicals methyl, ethyl, propyl, isopropyl, butyl, sec.-butyl and t-butyl. The term halogen as used herein includes the fluoro, chloro and bromo radicals.

The 2-azacycloalkylmethyl substituted tricyclic aryl ketones are readily reduced to their corresponding alcohols, which are also useful anticoagulants, by methods well known to those skilled in the art. Suitable reducing agents include metal hydride reducing agents, such as lithium aluminum hydride, with sodium borohydride having been found to be the reducing agent of choice. Two or more moles of sodium borohydride are generally used per mole of ketone reduced, the additional borohydride serving to neutralize the salts of the 2-azacycloalkylmethyl substituted tricyclic aryl ketones to their free base forms. The reaction is conducted in various organic solvents such as methanol, tetrahydrofuran or ethyl ether for periods ranging from a few minutes to about 24 hours. In general the reactants are mixed together at temperatures of 0°C. or below, whereupon the temperature is gradually allowed to increase to 30°C. Upon completion of the reaction, the reaction mixture is treated with water and the 2- azacycloalkylmethyl substituted tricyclic aryl alcohols are isolated and further purified by crystallization from an appropriate organic solvent.

The subclass of 2-pyrrolidinylmethyl and 2-piperidylmethyl tricyclic arylalkylene ketones are of particular interest inasmuch as they possess good anticoagulant activity and are readily prepared by condensation of the magnesium chelate with the 1-pyrroline trimer and 2,3,4,5-tetrahydropyridine trimer, respectively. This class of compounds is delineated in Formula (V) above, in which the symbol $n$ is the integer 3 or 4, $R_1$ and $X_{10}$ is hydrogen, and Y is the carbonyl radical.

Illustrative of specific base compounds which are encompassed by Formula (V) above are: 2-phenanthryl 2-piperidylmethyl ketone, 4-dibenzothienyl 2-piperidylmethyl ketone, 3-(9,10-dihydro)phenanthryl 2-piperidylmethyl ketone, 2-dibenzofuryl 2-pyrrolidinylmethyl ketone, 3-phenanthryl 2-pyrrolidinylmethyl ketone, 2-dibenzothienyl 2-pyrrolidinylmethyl ketone, 2-fluoroenyl 2-(hexahydro-1H-azepinylmethyl) ketone, 2-(5,5-dimethyl)pyrrolidinylmethyl 3-phenanthryl ketone, 2-(4-tert.-butyl)piperidylmethyl phenanthryl ketone, 2-dibenzofuryl 2-(6-ethyl)-piperidylmethyl ketone, α-(2-fluoroenyl)-2-piperidineethanol, α-(9-phenanthryl)-2-piperidineethanol, α-(2-dibenzofuryl)-2-piperidineethanol, α-(2-dibenzothienyl)2-pyrrolidineethanol, α-(3-phenanthryl)-2-pyrrolidineethanol, α-[3-(9,10-dihydro)-phenanthryl]-2-pyrrolidineethanol, 4-methyl-2-dibenzothienyl 2-piperidylmethyl ketone, 4-methoxy-2-dibenzofuryl 2-piperidylmethyl ketone and 7-ethyl-2-fluorenyl 2-piperidylmethyl ketone.

The expression "pharmaceutically acceptable acid addition salts" refers to any non-toxic organic or inorganic acid addition salt of the base compounds represented by Formula (V). Illustrative inorganic acids which form suitable salts include hydrochloric, hydrobromic, sulfuric, and phosphoric acids as well as acid metal salts such as sodium monohydrogen orthophosphate and potassium hydrogen sulfate. Illustrative organic acids which form suitable salts include the mono, di and tricarboxylic acids. Illustrative of such acids are, for example, acetic, propionic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methanesulfonic acid and 2-hydroxyethanesulfonic acid. Either the mono or the di-acid salts can be formed, and such salts can be utilized in either a hydrated or a substantially anhydrous form.

The novel compounds of the present invention, including their acid addition salts, isomers and corresponding carbinols, are useful anticoagulants. Arterial thrombosis, particularly when it affects those arteries supplying the heart muscle and brain, is a leading cause of death and disability. The novel compounds of this invention prevent blood coagulation by preventing the aggregation of blood platelets. Blood platelets play a dominant role in thrombotic conditions, both in the initial event and at the occlusive stage. Hence compounds which inhibit platelet aggregation are of importance in the treatment of thrombotic diseases. These compounds can be administered to animals, mammals and humans, either per se or in combination with conventional pharmaceutical carriers in various dosage unit forms. Suitable dosage unit forms include oral preparations such as tablets, capsules, powders, granules, oral solutions and suspensions, sublingual and intrabuccal preparations, as well as parenteral dosage unit forms which are useful for subcutaneous, intramuscular or intravenous administration. The quantity of active ingredient administered can vary over a wide range so as to provide from about 1.0 mg/kg to about 100 mg/kg of body weight per day in order to achieve the desired effect. Each unit dose can contain from about 5 to 500 mg of the active ingredient in combination with the pharmaceutical carrier. Such doses may be administered from 1 to 4 times daily.

In preparing solid compositions such as tablets, the principal active ingredient is mixed with conventional pharmaceutical excipients such as gelatin, starches, lactose, magnesium stearate, talc, acacia, dicalcium phosphate and functionally similar materials. Tablets can be laminated, coated or otherwise compounded to provide for a prolonged or delayed action and to release a predetermined successive amount of medication. Capsules are prepared by mixing the active ingredient with an inert pharmaceutical filler or diluent and filled in either hard gelatin capsules or machine encapsulated soft gelatin capsules. Syrups or elixirs can contain the active ingredients together with sucrose or other sweetening agents, methyl and propyl parabens as preservatives, and suitable coloring and flavoring agents.

Parenteral fluid dosage forms are prepared by utilizing the active ingredient in a sterile liquid vehicle, the preferred vehicle being water or a saline solution. Compositions having the desired clarity, stability and adaptability for parenteral use are obtained by dissolving from about 0.1 mg to about 3 grams of the active ingredient in a vehicle consisting of a mixture of nonvolatile liquid polyethylene glycols which are soluble in both water and organic liquids, and which have molecular weights ranging from about 200 to about 1500. Such solutions may advantageously contain suspending agents, such as sodium carboxymethylcellulose, methylcellulose, polyvinylpyrrolidone or polyvinyl alcohol. Additionally, they may contain bactericidal and fungicidal agents, as for example, parabens, benzyl alcohol, phenol or thimerosal. If desired, isotonic agents can be included, such as sugar or sodium chloride, as well as local anesthetics, stabilizing or buffering agents. In order to further enhance stability, the parenteral compositions may be frozen after filling and water removed by freeze-drying techniques well known in the art, enabling such dry, lyophilized powders to be reconstituted immediately prior to their use.

EXAMPLE I 2,3,4,5-Tetrahydropyridine Trimer

To 170 g (2.0 moles) of piperidine is added 120 g (2.0 moles) of acetic acid via dropwise addition at a temperature below 10°C. The resulting solution is added dropwise over a period of 1 hour to an aqueous solution containing 2.2 moles of $Ca(ClO)_2$ while maintaining the temperature of the reaction mixture at 0° to −5°C. Stirring is continued for an additional 15 minutes, and the mixture is extracted with ether. The ether extracts are combined, dried over anhydrous $Na_2SO_4$ and most of the solvent removed. (Caution! N-chloropiperidine tends to decompose spontaneously.) Approximately 200 ml of ether is permitted to remain and temperatures in excess of 60°C. are avoided. The remaining ether solution is added over a period of 2.5 hours in dropwise fashion to a vigorously stirred, refluxing solution containing 264 g (4.0 moles) of potassium hydroxide in 1250 ml of anhydrous ethyl ether. Stirring is continued for 2 hours and the mixture is allowed to remain at room temperature during which the 2,3,4,5-tetrahydropyridine is trimerized. The potassium chloride which precipitates is removed by filtration, washed with anhydrous ethanol, and the ethanol removed from the filtrate by distillation. The residue is dissolved in 750 ml of water, the potassium chloride previously collected is added, and the solution extracted with ether. The combined ether extracts are dried ($MgSO_4$) and the solvent removed by evaporation. Recrystallization of the residue from acetone yields 2,3,4,5-tetrahydropyridine as the α-trimer having a M.P. of 58°–61°C. The β-isomer (M.P. 40°–68°C.) can be converted to the more stable α-isomer by recrystallization from acetone containing 2% water. The material so prepared is stored in a closed container over potassium hydroxide and is stable for over 1 year.

EXAMPLE II

1-Pyrroline Trimer

To 140.3 g (1.05 moles) of N-chlorosuccinimide is added a solution of 71.1 g (1 mole) of pyrrolidine dissolved in 1 l of ethyl ether. The mixture is stirred at room temperature under $N_2$ for 24 hours and sufficient water added to dissolve the solids. The ether phase is separated, dried over anhydrous sodium sulfate and the solvent evaporated under nitrogen. (Caution! N-chloropyrrolidine tends to decompose spontaneously.) Approximately 100 ml of ether are permitted to remain and temperatures in excess of 60°C. are avoided. The remaining ether solution is added over a period of 1½ hours in dropwise fashion to a vigorously stirred, ice-cooled solution of 2N methanolic potassium hydroxide. Stirring is continued for 1 hour and the methanol removed at a temperature of 25°–30°C. at a reduced pressure of approximately 200 mm. Water is added to the remaining residue and the resulting mixture is subjected to continuous extraction with ethyl ether. The ether extract is separated and distilled under nitrogen at atmospheric pressure. Fractions having a B.P. 81°–90°C. and 91°–97°C. were collected, the latter fraction warming spontaneously, presumably due to exothermic trimerization. Both fractions are capable of condensation with MMC chelates of methyl ketones.

EXAMPLE III

1-Adamantyl-2-piperidylmethyl ketone

Magnesium methyl carbonate (1 mole, 1.5 N in dimethylformamide) is heated to 120°C. in an atmosphere of carbon dioxide and 37.2 g (0.208 mole) of 1-adamantyl methyl ketone added. The mixture is stirred at this temperature for 4 hours under a stream of nitrogen allowing the methanol that is formed to escape. The reaction mixture is cooled under carbon dioxide and 21.0 g (0.25 mole) of 2,3,4,5-tetrahydropyridine added. The reaction mixture is stirred at room temperature under carbon dioxide for 70 hours, poured into a hydrochloric acid-ice mixture and collected by filtration. This procedure results only in a 6% yield.

To overcome steric hindrance the procedure is repeated with the following modifications. The 1-adamantyl methyl ketone is added to the MMC solution in the same manner and at the same temperature, but stirred for a period of 28 hours under a stream of nitrogen instead of 4 hours. The mixture is cooled to room temperature in an atmosphere of carbon dioxide, 2,3,4,5-tetrahydropyridine added, and the mixture stirred at room temperature under carbon dioxide for a period of 5 days. The 1-adamantyl-2-piperidylmethyl ketone prepared in this manner is obtained in 37% yield as the hydrochloride salt and when recrystallized twice from isopropanol has a M.P. of 239–40°C.

Following essentially the same procedure but substituting cyclohexyl methyl ketone for the 1-adamantyl methyl ketone above results in the formation of cyclohexyl 2-piperidylmethyl ketone as the hydrochloride salt.

EXAMPLE IV

2′,5′-Dimethoxy-2-(2-piperidyl)acetophenone

Magnesium methyl carbonate (approximately 1 mole of a 2 M solution in dimethylformamide) is heated to 120°C. under an atmosphere of carbon dioxide and 45.0 g (0.25 mole) of 2′,5′-dimethoxyacetophenone added thereto. Nitrogen is substituted for the carbon dioxide and the mixture is stirred at 120°C. for 5 hours while allowing the methanol that forms to escape. The mixture is cooled under carbon dioxide and 25.3 g (0.30 mole) of 2,3,4,5-tetrahydropyridine (as the trimer, α-tripiperidein) added. The resulting mixture is stirred at room temperature in an atmosphere of carbon dioxide for 40 hours, poured into 3 liters of ethyl ether and the resulting precipitate is collected by filtration. The filtrate is acidified with a mixture of 300 ml of concentrated HCl-ice and the resulting precipitate is collected by filtration. The filtrate is made alkaline with 2N NaOH, extracted with ethyl ether, the extracts dried ($Na_2SO_4$) and the solvent removed. The resulting oily residue is converted to the hydrochloride salt by the addition of isopropanolic HCl. The two portions are combined and recrystallized from isopropanolwater to yield 56.0 g (75% of theory) of 2′,5′-dimethoxy-2-(2-piperidyl)acetophenone as the hydrochloride salt having a M.P. of 186°–188°C. (dec.)

EXAMPLE V

4′-Dodecyl-2-(2-piperidyl)acetophenone

Magnesium methyl carbonate (0.5 mole 1 M in dimethylformamide) is heated to 120°C. under an atmosphere of carbon dioxide. The compound 4′-dodecylacetophenone, 28.9 g (0.1 mole), is added, and the mixture stirred at 120°C. for 4 hours under a stream of nitrogen, allowing the methanol that forms to escape. The reaction mixture is cooled to room temperature under an atmosphere of carbon dioxide and 10.1 g (0.12 mole) of 2,3,4,5-tetrahydropyridine trimer (α-tripiperidein) is added. The mixture is stirred at room temperature for 66 hours in an atmosphere of carbon dioxide and poured into a solution 800 ml of 2N HCl. The solid is removed by filtration, dissolved in methylene dichloride, dried over anhydrous sodium sulfate and azeotroped with methyl ether until the product precipitates. The 4′-dodecyl-2-(2-piperidyl)acetophenone, when recrystallized as the hydrochloride salt from a methylene dichloride-ethyl ether mixture, is obtained in 80% yield, (32.5 g) and has a M.P. of 126–7°C.

EXAMPLE VI

4'-Phenethyl-2-(2-pyrrolidinyl)acetophenone

Magnesium methyl carbonate (0.4 mole, 2 M in dimethylformamide) is heated to 120°C. under carbon dioxide. The compound 4'-phenethylacetophenone, 22.4 g (0.1 mole), is added and the mixture is stirred at 120°C. for 4 hours under a stream of nitrogen allowing the methanol that forms to escape. The reaction mixture is allowed to cool to room temperature under an atmosphere of carbon dioxide and 8.3 g (0.12 mole) of 1-pyrroline (as the trimer) added and stirred at room temperature under carbon dioxide for a period of 40 hours. The solution is poured into a mixture of 200 ml of concentrated HCl and 800 g of ice and the product removed by filtration. The 4'-phenethyl-2-(2-pyrrolidinyl)-acetophenone when twice recrystallized in the form of its hydrochloride salt from an aqueous isopropanol solution is obtained in 63% yield (20.1 g) and has a M.P. of 200–1°C. (dec).

EXAMPLE VII

5-Methyl-6-phenyl-1-(2-piperidyl)-3,5-hexadien-2-one

Magnesium methyl carbonate (1.2 moles, 2 N in dimethylformamide) is heated to 120°C. under an atmosphere of carbon dioxide. The compound 5-methyl-6-phenyl-3,5-hexadien-2-one, 53.0 g (0.285 mole) is added and the mixture is stirred at 120°C. for a period of 4 hours under a stream of nitrogen while permitting the methanol that forms to escape. The mixture is allowed to cool under an atmosphere of carbon dioxide and 57.0 g (0.68 mole) of 2,3,4,5-tetrahydropyridine (as α-tripiperidein) is added and stirred at room temperature under an atmosphere of carbon dioxide for a period of 70 hours. The reaction mixture is poured into a concentrated HCl-ice mixture and extracted with methylene dichloride. The extracts are combined, washed with water, dried over anhydrous sodium sulfate, and the solvent removed. The crude 5-methyl-6-phenyl-1-(2-piperidyl)-3,5-hexadein-2-one which remains is recrystallized twice from isopropyl alcohol as the hydrochloride salt and is obtained in 48% yield (41.6 g) and has a M.P. of 179–80°C.

EXAMPLE VIII

1-(2,6-Diethylphenyl)pyrrol-2-yl 2-piperidylmethyl ketone

A mixture of 186 g (0.5 mole) of magnesium methyl carbonate reagent (2.69 millimoles/g) and 300 ml of dry dimethylformamide are heated to 120°C. under an atmosphere of carbon dioxide. The compound 1-(2,6-diethylphenyl)pyrrol-2-yl methyl ketone, 36.1 g (0.15 mole), is added and the mixture stirred at 120°C. for a period of 4 hours under a stream of nitrogen to form the chelate, allowing the methyl alcohol that forms to escape. The mixture is cooled to room temperature under an atmosphere of carbon dioxide and 15.1 g (0.18 mole) of 2,3,4,5-tetrahydropyridine (as α-tripiperidein) is added and stirring continued at room temperature for a period of 40 hours under an atmosphere of carbon dioxide. The reaction mixture is poured into a solution of 2 N hydrochloric acid and extracted with ethyl ether. The combined extracts are washed with water, dried over sodium sulfate and the solvent removed. The remaining aqueous phase is made alkaline using a solution of 2 N sodium carbonate and extracted with ethyl ether. The ether extract is washed, dried over sodium sulfate and the solvent removed. The residue is converted to the hydrochloride salt, triturated with ether to solidify and the crude 1-(2,6-diethylphenyl)pyrrol-2-yl 2-piperidylmethyl ketone recrystallized from a methylene dichloride-ethyl ether mixture to yield 16.4 g (30% yield) of a product having a M.P. of 162–4°C.

EXAMPLE IX

1,1-Diphenyl-3-(2-piperidyl)propan-2-one

Magnesium methyl carbonate (1.2 moles, 2 N in dimethylformamide) is heated to 120°C. under an atmosphere of carbon dioxide. The compound 1,1-diphenylacetone, 63.0 g (0.3 moles), is added and the mixture is stirred at 120°C. for a period of 4 hours under a stream of nitrogen to form the chelate, allowing the methyl alcohol that forms to escape. The mixture is cooled to room temperature under an atmosphere of carbon dioxide and 30.0 g (0.36 moles) of 2,3,4,5-tetrahydropyridine (as α-tripiperidein) is added and stirring continued at room temperature for a period of 6 days under an atmosphere of carbon dioxide. The reaction mixture is poured into 375 ml of concentrated HCl on 400 g of ice and the resulting mixture is extracted with methylene dichloride. The extracts are combined, dried over anhydrous sodium sulfate and the solvent is removed. The crude oil is recrystallized twice from an aqueous isopropyl alcohol solution to yield 37.9 g (37% yield) of 1,1-diphenyl-3-(2-piperidyl)propan- 2-one as the hydrochloride salt having a M.P. of 197–9°C. (dec.)

EXAMPLE X

4'-(Fluoren-9-ylidenemethyl)-2-(2-piperidyl)acetophenone

Magnesium methyl carbonate (approximately 0.4 mole in 1 M solution in dry dimethylformamide) is heated to 120°C. under a stream of carbon dioxide and 25.0 g (0.084 mole) of 4'-fluoren-9-ylidenylmethylacetophenone added. Nitrogen is substituted for the carbon dioxide and the mixture is stirred at 120°C. for 4 hours while allowing the methanol that forms to escape. The reaction mixture is again placed under dry carbon dioxide and allowed to cool to room temperature, whereupon 7.9 g (0.096 mole of monomer) of α-tripiperideine is added as a finely ground powder. The mixture is stirred under carbon dioxide at room temperature for 2–3 days and is then poured into approximately 1 liter of 3 N HCl. After about 3 hours of vigorous stirring a solid is obtained which is removed by filtration and washed with 2 N HCl followed by a wash of ethyl ether. The 4'-(fluoren-9-ylidenemethyl)-2-(2-piperidyl)acetophenone so prepared is recrystallized twice from an aqueous isopropanol solution and is obtained in 73% yield (25.3 g) and has a M.P. of 223.5°–224.0°C. (dec.)

EXAMPLE XI

2-Dibenzofuranyl 2-piperidylmethyl ketone

Magnesium methyl carbonate (0.6 mole, 2.5 N in dimethylformamide) is heated to 120°C. under an atmosphere of carbon dioxide. The compound 2-acetyldibenzofuran, 31.5 g (0.15 mole) is added and the mixture is stirred at 120°C. for a period of 4 hours under a stream of nitrogen to form the chelate, allowing the methyl alcohol that forms to escape. The mixture is cooled to room temperature under an atmosphere of carbon dioxide and 15.2 g (0.18 mole) of 2,3,4,5-tetrahydropyridine (as α-tripiperidine) is added and the mixture stirred at room temperature for a period of 40 hours in an atmosphere of carbon dioxide. The resulting mixture is poured into 200 ml of concentrated HCl on 600 g of ice. After standing for 48 hours the precipitate which forms is filtered and washed with ethyl ether. The 2-dibenzofuranyl-2-piperidylmethyl ketone so prepared is twice recrystallized from isopropyl alcohol as the hydrochloride salt and is obtained in 32% yield (16.0 g) and has a M.P. of 218–20°C. (dec.)

EXAMPLE XII

2-Fluorenyl 2-piperidylmethyl ketone

Following essentially the same procedure as in Example XI, but substituting 2-acetylfluorene for the 2-acetyldibenzofuran above results in the formation of 2-fluorenyl 2-piperidylmethyl ketone as the hydrochloride salt, and which when recrystallized from isopropyl alcohol has a M.P. of 222–3°C.

EXAMPLE XIII

Dibenzothiophen-2-yl 2-piperidylmethyl ketone

Following essentially the same procedure as in Example XI, but substituting 2-acetyldibenzothiophene for the 2-acetyldibenzofuran above results in the formation of dibenzothiophen-2-yl 2-piperidylmethyl ketone as the hydrochloride salt, and which when recrystallized from isopropyl alcohol has a M.P. of 210–12°C. (dec.)

EXAMPLE XIV

2-Dibenzofuranyl 2-pyrrolidinylmethyl ketone

Following essentially the same procedure as in Example XI, but substituting 1-pyrroline for the 2,3,4,5-tetrahydropyridine (as α-tripiperidein) above results in the formation of 2-dibenzofuranyl 2-pyrrolidinylmethyl ketone as the hydrochloride salt.

EXAMPLE XV

3-Phenanthryl 2-piperidylmethyl ketone

Following essentially the same procedure as in Example XI, but substituting 3-acetylphenanthrene for the 2-acetyldibenzofuran above results in the formation of 3-phenanthryl 2-piperidylmethyl ketone as the hydrochloride salt, and which when recrystallized from isopropyl alcohol has a M.P. of 190–2°C. (dec.)

EXAMPLE XVI

2-Fluorenyl 2-pyrrolidinylmethyl ketone

Following essentially the same procedure as in Example XI above, but substituting 2-acetylfluorene for the 2-acetyldibenzofuran above and substituting 1-pyrroline as the trimer for the 2,3,4,5-tetrahydropyridine (as α-tripiperidein) above results in the formation of 2-fluorenyl 2-pyrrolidinylmethyl ketone as the hydrochloride salt, and which when recrystallized from isopropyl alcohol has a M.P. of 234–44°C. (dec.)

EXAMPLE XVII

9-Phenanthryl 2-piperidylmethyl ketone

Following essentially the same procedure as in Example XI, but substituting 9-acetylphenanthrene for the 2-acetyldibenzofuran above results in the formation of 9-phenanthryl 2-piperidylmethyl ketone as the hydrochloride salt, and which when recrystallized from isopropyl alcohol has a M.P. of 215–6°C.

EXAMPLE XVIII

α-(3-Phenanthryl)-2-piperidineethanol glycolate

To a suspension of 3.7 g (0.098 mole) of sodium borohydride in 200 ml of absolute ethanol is slowly added over a period of 30 minutes 11.2 g (0.033 mole) of 3-phenanthryl 2-piperidylmethyl ketone as the hydrochloride salt. The resulting mixture is stirred overnight at room temperature and poured into 800 ml of water. The product is extracted from the diluted reaction mixture with ether, and the ether extract is washed with three portions of a 10% aqueous acetic acid solution. The acid washes are combined and made alkaline using a 2 N sodium hydroxide solution. The product is rer-extracted into ether, the extracts combined, dried over anhydrous sodium sulfate and the solvent removed by evaporation. The residue is dissolved in isopropanol, and a solution of 2.6 g (0.035 mole) of glycolic acid in isopropanol is added to crystallize the product as the glycolate salt. The α-(3-phenanthryl)-2-piperidineethanol glycolate is separated by fractional recrystallization into the two pairs of diastereoisomers, having a M.P. of 172–6°C. (dec.) and 177–9°C. (dec.), respectively.

Following essentially the same procedure but substituting dibenzothiophen-2-yl 2-piperidylmethyl ketone for the 3-phenanthryl 2-piperidylmethyl ketone above, results in the formation of α-(dibenzothiophen-2-y)-2-piperidineethanol glycolate having a M.P. of 192–4°C. (dec.)

Following essentially the same procedure but substituting 2-fluorenyl 2-pyrrolidinylmethyl ketone for the 3-phenanthryl 2-piperidylmethyl ketone and further substituting maleic acid for the glycolic acid, results in the preparation of α-(2-fluorenyl)-2-pyrrolidineethanol as the maleate salt having a M.P. of 147–9°C. (dec.)

EXAMPLE XIX

The anticoagulant activity of the compounds of this invention is determined by the inhibition of platelet (white thrombus) aggregation, which is the initial phase involved in the coagulation of blood. Platelet-rich plasma (PRP) obtained from a human volunteer, having a platelet count of approximately 400,000/mm$^3$ is aggregated using approximately 2 micrograms of adenosine diphosphate per ml of PRP. Quantitative platelet aggregation measurements are made using a photometer connected to an automatic recorder which measures the changes in optical clarity of a standard cell containing the test solution. As the platelets aggregate, light transmission increases and thus both the rate of aggregation and the degree of aggregation can be determined. In this fashion, adenosine diphosphate induced aggregation of platelet-rich plasma is compared under identical circumstances to a corresponding aliquot containing a dilute solution of the test compound. The results are expressed as a percent inhibition.

Following this procedure the compound 2-fluorenyl 2-piperidylmethyl ketone hydrochloride at a concentration of 100 and 30 micrograms/milliliters, demonstrates an in vitro inhibition of adenosine diphosphate induced platelet aggregation in human platelet-rich plasma of 100% and 38%, respectively.

EXAMPLE XX

Preparation of a tablet formulation

One thousand tablets for oral use, each containing 25 mg of 2-fluorenyl 2-piperidylmethyl ketone hydrochloride are prepared according to the following formulation:

|     |                                      | Grams |
|-----|--------------------------------------|-------|
| (a) | 2-fluorenyl 2-piperidylmethyl ketone hydrochloride | 25 |
| (b) | Dicalcium phosphate                  | 150   |
| (c) | Methylcellulose, U.S.P. (15 cps)     | 6.5   |
| (d) | Talc                                 | 20    |
| (e) | Calcium stearate                     | 2.5   |

The 2-fluorenyl 2-piperidylmethyl ketone hydrochloride and dicalcium phosphate are mixed well, granulated with a 7.5% aqueous solution of methylcellulose, passed through a No. 8 screen and carefully dried. The dried granules are passed through a No. 12 screen, blended with talc and calcium stearate and compressed into tablets.

EXAMPLE XXI

Preparation of a capsule formulation

One thousand two-piece hard gelatin capsules for oral use each containing 100 mg of 2-fluorenyl 2-piperidylmethyl ketone hydrochloride are prepared from the following ingredients:

|     |                                      | Grams |
|-----|--------------------------------------|-------|
| (a) | 2-fluorenyl 2-piperidylmethyl ketone hydrochloride | 100 |
| (b) | Lactose, U.S.P.                      | 100   |
| (c) | Starch, U.S.P.                       | 10    |
| (d) | Talc, U.S.P.                         | 5     |
| (e) | Calcium stearate                     | 1     |

The finely powdered materials are mixed until uniformly dispersed and filled into hard shelled gelatin capsules of the appropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

EXAMPLE XXII

Preparation of a parenteral solution

A sterile aqueous suspension suitable for parenteral use is prepared from the following ingredients:

|     |                                      | Grams |
|-----|--------------------------------------|-------|
| (a) | 2-fluorenyl 2-piperidylmethyl ketone hydrochloride | 1 |
| (b) | Polyethylene glycol 4000, U.S.P.     | 3     |
| (c) | Sodium chloride                      | 0.9   |
| (d) | Polyoxyethylene derivatives of sorbitan monooleate (TWEEN 80) U.S.P. | 0.4 |
| (e) | Sodium metabisulfite                 | 0.1   |
| (f) | Methylparaben, U.S.P.                | 0.18  |
| (g) | Propylparaben, U.S.P.                | 0.02  |
| (h) | Water for injection q.s. to 100 ml   |       |

The parabens, sodium metabisulfide, and sodium chloride are dissolved in approximately one-half the volume of water for injection at 80°C. with stirring. The solution is cooled to below 40°C. and the active ingredient is dissolved therein followed by the polyethylene glycol 4,000 and the polyoxyethylene derivatives of sorbitan monooleate. The cooled solution is adjusted to the final volume with water for injection and is then sterilized by sterile filtration through a suitable filter. Each one ml of solution contains 10 mg of 2-fluorenyl 2-piperidylmethyl ketone hydrochloride.

We claim:

1. A process of preparing 2-azacycloalkylmethyl ketones having the formula:

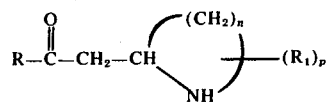

wherein $n$ is an integer of from 3 to 5, $p$ is an integer of from 1 to 2, R is a neutral organic radical selected from the group consisting of alkyl, alkenyl, carbocycle furanyl, pyrrolyl, benzothienyl, pyrazolyl, oxazolyl, benzimidazolyl, dibenzofuranyl and dibenzothienyl, $R_1$ is hydrogen or lower alkyl having from 1 to 4 carbon atoms which comprises heating a solution of a methyl ketone having the formula

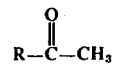

with an excess of magnesium methyl carbonate to form a magnesium chelate; cooling the reaction mixture and reacting said chelate solution in an atmosphere of carbon dioxide with a 1-azacycloalkene having the formula:

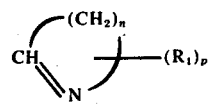

and isolating the product therefrom.

2. A process of claim 1 in which the 1-azacycloalkene is 2,3,4,5-tetrahydropyridine.

3. A process of claim 1 in which the 1-azacycloalkene is 1-pyrroline.

4. A process according to claim 1 of preparing 2-azacycloalkylmethyl ketones having the formula:

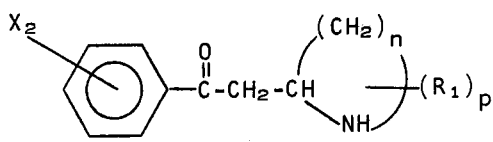

wherein $n$ is an integer of from 3 to 5, $p$ is an integer of from 1 to 2, $R_1$ is hydrogen or lower alkyl having from 1 to 4 carbon atoms, $X_2$ is selected from the group consisting of phenyl, halophenyl, trifluoromethylphenyl, alkoxyphenyl having from 1 to 4 carbon atoms, alkylthiophenyl having from 1 to 4 carbon atoms, phenoxy, halophenoxy, trifluoromethylphenoxy, alkoxyphenoxy, having 1 to 4 carbon atoms, alkylthiophenoxy having 1 to 4 carbon atoms, phenylthio, phenylalkyl having from 1 to 4 carbon atoms, phenylvinyl, phenylalkoxy having from 2 to 4 carbon atoms, and phenoxyalkoxy having from 2 to 4 carbon atoms, which comprises heating a solution of a methyl ketone having the formula

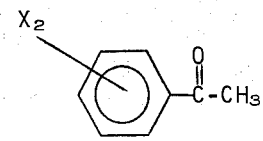

with an excess of magnesium methyl carbonate to form a magnesium chelate; cooling the reaction mixture and reacting said chelate solution in an atmosphere of carbon dioxide with a 1-azacycloalkene having the formula

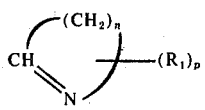

and isolating the product therefrom.

5. A process according to claim 1 of preparing 2-azacycloalkylmethyl ketones having the formula:

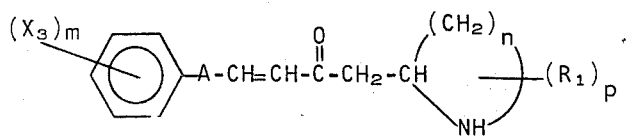

wherein $n$ is integer of from 3 to 5, $p$ is an integer of from 1 to 2, $R_1$ is hydrogen or lower alkyl having from 1 to 4 carbon atoms, $m$ is an integer of from 1 to 3, $X_3$ is selected from the group consisting of hydrogen, lower alkyl having from 1 to 6 carbon atoms, alkoxy having from 1 to 6 carbon atoms, alkylthio having from 1 to 6 carbon atoms, halogen, trifluoromethyl and phenyl, A is a sigma bond or selected from the group of radicals consisting of vinylidene and propenylidene, which comprises heating a solution of a methyl ketone having the formula

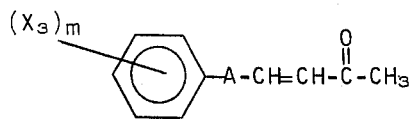

with an excess of magnesium methyl carbonate to form a magnesium chelate; cooling the reaction mixture and reacting said chelate solution in an atmosphere of carbon dioxide with a 1-azacycloalkene having the formula

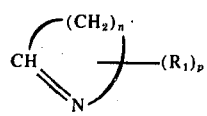

and isolating the product therefrom.

6. A process according to claim 1 of preparing 2-azacycloalkylmethyl ketones having the formula:

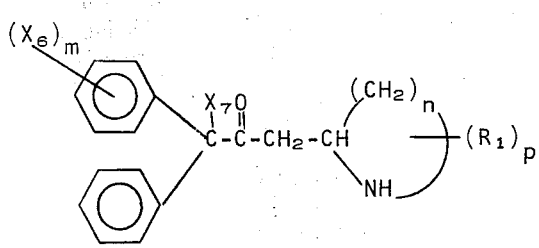

wherein $n$ is an integer of from 3 to 5, $p$ is an integer of from 1 to 2, $R_1$ is hydrogen or lower alkyl having from 1 to 4 carbon atoms, $m$ is an integer of from 1 to 3, $X_6$ is selected from the group consisting of hydrogen, lower alkyl having from 1 to 4 carbon atoms, lower alkoxy having from 1 to 4 carbon atoms, alkylthio having from 1 to 4 carbon atoms and halogen, $X_7$ is selected from the group consisting of hydrogen and lower alkyl having from 1 to 4 carbon atoms, which comprises heating a solution of a methyl ketone having the formula

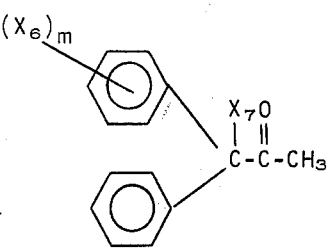

with an excess of magnesium methyl carbonate to form a magnesium chelate; cooling the reaction mixture and reacting said chelate solution in an atmosphere of carbon dioxide with a 1-azacycloalkene having the formula

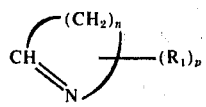

and isolating the product therefrom.

7. A 2-azacycloalkylmethyl derivative having the formula:

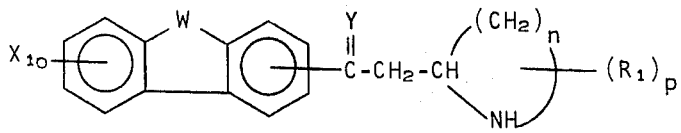

wherein n is an integer of from 3 to 5; p is an integer of from 1 to 2; $R_1$ is hydrogen or lower alkyl having from 1 to 4 carbon atoms; $X_{10}$ is selected from the group consisting of hydrogen, lower alkyl having from 1 to 4 carbon atoms, lower alkoxy having from 1 to 4 carbon atoms and halogen; Y represents the radicals

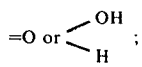

W is selected from the group of radicals consisting of —O—, —S—, —CH$_2$—, —CH=CH— and —CH$_2$CH$_2$—; and the pharmaceutically acceptable acid addition salts thereof.

8. A compound of claim 7 wherein n is an integer of from 3 to 4; $R_1$ and $X_{10}$ are both hydrogen; and Y is the radical =O.

9. A compound of claim 7 which is 2-fluorenyl 2-piperidylmethyl ketone and its pharmaceutically acceptable acid addition salts.

10. A compound of claim 7 which is α-(3-phenanthryl)-2-piperidineethanol and its pharmaceutically acceptable acid addition salts.

11. A process according to claim 1 of preparing 2-azacycloalkylmethyl ketones having the formula:

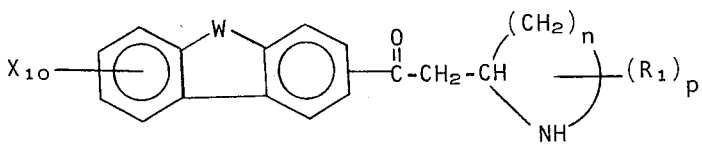

wherein n is an integer of from 3 to 5, p is an integer of from 1 to 2, $R_1$ is hydrogen or lower alkyl having from 1 to 4 carbon atoms, $X_{10}$ is selected from the group consisting of hydrogen, lower alkyl having from 1 to 4 carbon atoms, lower alkoxy having from 1 to 4 carbon atoms and halogen, W is selected from the group of radicals consisting of O—, —S—, —CH$_2$—, —CH=CH— and —CH$_2$CH$_2$—, which comprises heating a solution of a methyl ketone having the formula

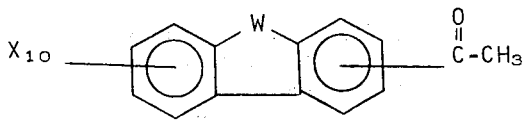

with an excess of magnesium methyl carbonate to form a magnesium chelate; cooling the reaction mixture and reacting said chelate solution in an atmosphere of carbon dioxide with a 1-azacycloalkene having the formula

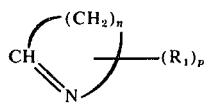

and isolating the product therefrom.

* * * * *

UNITED STATES PATENT AND TRADEMARK OFFICE
CERTIFICATE OF CORRECTION

PATENT NO. : 3,931,155
DATED : January 6, 1976
INVENTOR(S) : J. Martin Grisar and George P. Claxton It is certified that error appears in the above-identified patent and that said Letters Patent are hereby corrected as shown below:

Column 5, line 43, "anhyride" should read "anhydride"; Column 6, lines 55-56, "-CH=CH-CH=λCH-" should read "-CH=CH-CH=CH-"; Column 9, line 61, "are" should read "as"; Column 17, line 3, "tripiperidine" should read "tripiperidein"; Column 17, line 61, "234-44°C." should read "243-44°C."; Column 18, line 31, "dibenzothiophen-2-y" should read "dibenzothiophen-2-yl"; Column 19, line 64, "metabisulfide" should read "metabisulfite"; Column 24, lines 5-6, "-CH=λCH-" should read "-CH=CH-".

Signed and Sealed this

Sixteenth Day of November 1976

[SEAL]

Attest:

RUTH C. MASON
*Attesting Officer*

C. MARSHALL DANN
*Commissioner of Patents and Trademarks*